United States Patent [19]

Chakrabarti et al.

[11] Patent Number: 4,492,699
[45] Date of Patent: Jan. 8, 1985

[54] TRIAZOLOBENZODIAZEPINE DERIVATIVES

[75] Inventors: Jiban K. Chakrabarti, Camberley; Terrence M. Hotten, Farnborough; David J. Steggles, Bracknell, all of England

[73] Assignee: Lilly Industries Limited, London, England

[21] Appl. No.: 541,605

[22] Filed: Oct. 13, 1983

Related U.S. Application Data

[62] Division of Ser. No. 327,143, Dec. 3, 1981, Pat. No. 4,431,589.

[30] Foreign Application Priority Data

Dec. 11, 1980 [GB] United Kingdom ............... 8039659

[51] Int. Cl.³ .................. A61K 31/495; C07D 487/04
[52] U.S. Cl. .................................. 424/250; 260/243.3
[58] Field of Search ............... 260/243.3, 239.3 T; 544/366; 424/250

[56] References Cited

U.S. PATENT DOCUMENTS

| | | | |
|---|---|---|---|
| 3,450,694 | 6/1969 | Swett et al. | 260/239.3 |
| 3,474,099 | 10/1969 | Renz et al. | 260/268 |
| 3,641,031 | 2/1972 | Schindler et al. | 260/268 TR |
| 3,758,479 | 9/1973 | Schmutz et al. | 260/268 TR |
| 3,761,481 | 9/1973 | Nakanishi et al. | 260/268 TR |
| 3,793,325 | 2/1974 | Schmutz et al. | 260/268 TR |
| 3,813,395 | 5/1974 | Nakanishi et al. | 260/268 TR |
| 3,842,082 | 10/1974 | Hunziker | 260/268 TR |
| 3,951,981 | 4/1976 | Safir | 260/268 TR |
| 3,953,430 | 4/1976 | Safir | 260/239.3 |
| 3,962,248 | 6/1976 | Schneider | 260/268 TR |
| 4,115,568 | 9/1978 | Chakrabarti et al. | 424/250 |
| 4,115,574 | 9/1978 | Chakrabarti et al. | 424/250 |
| 4,172,831 | 10/1979 | Chakrabarti et al. | 260/239.3 T |
| 4,317,823 | 3/1982 | Rainer | 424/248.54 |
| 4,337,198 | 6/1982 | Sorg et al. | 260/243.3 |
| 4,404,137 | 9/1983 | Chakrabarti et al. | 260/239.30 T |

FOREIGN PATENT DOCUMENTS

| 3016 | 7/1979 | European Pat. Off. |
| 2707270 | 8/1978 | Fed. Rep. of Germany |

OTHER PUBLICATIONS

Indian J. Chem., 14B, 394–396 (1976).
Derwent 21412 D/12.
J. Heterocyclic Chemistry, 16, 935 (1979).

Primary Examiner—Paul M. Coughlan, Jr.
Assistant Examiner—Cecilia Shen
Attorney, Agent, or Firm—Charles W. Ashbrook; Arthur R. Whale

[57] ABSTRACT

These are described compounds of formula (I)

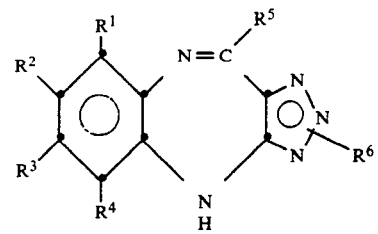

or an acid addition salt thereof; in which $R^1$, $R^2$, $R^3$ and $R^4$ independently represent hydrogen, $C_{1-4}$ alkyl, $C_{2-4}$ alkenyl, halogen, $C_{1-4}$ haloalkyl, nitro, $C_{1-4}$ alkoxy, $C_{1-4}$ haloalkoxy, $C_{1-4}$ alkylthio or phenylsulphonyl; in which $R^5$ is a group of the formula

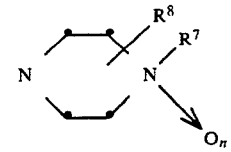

where $R^7$ is hydrogen or $C_{1-6}$ alkyl, $R^8$ is hydrogen or $C_{1-4}$ alkyl and n is 0 or 1, provided that when $R^7$ is hydrogen n is 0; and in which $R^6$ is attached to the 1, 2 or 3 position of the triazole ring and is hydrogen, $C_{1-10}$ alkyl, $C_{3-7}$ cycloalkyl, $C_{3-7}$ cycloalkyl $C_{1-4}$ alkyl, phenyl, benzyl or acyl. These compounds are pharmaceutically active and are especially useful in the treatment of disorders of the central nervous system. They are prepared by reacting an amine of formula $R^5H$ with a triazolobenzodiazepine intermediate appropriately substituted at the 10-position or by ring-closing the appropriate anilinotriazole.

7 Claims, No Drawings

TRIAZOLOBENZODIAZEPINE DERIVATIVES

This application is a division of application Ser. No. 327,143, filed Dec. 3, 1981, now U.S. Pat. No. 4,431,589.

This invention relates to novel compounds, processes for preparing them and their use as pharmaceuticals.

Various tricyclic compounds with pharmaceutical properties have already been investigated and these have been mainly of the type that comprise two benzene nuclei. We have now discovered a new group of compounds having the following basic structure

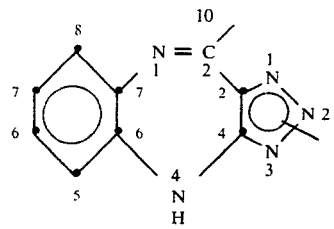

The compounds of the invention are of the following formula (I)

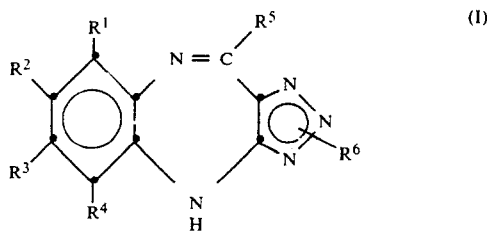

or an acid addition salt thereof; in which $R^1$, $R^2$, $R^3$ and $R^4$ independently represent hydrogen, $C_{1-4}$ alkyl, $C_{2-4}$ alkenyl, halogen, $C_{1-4}$ haloalkyl, nitro, $C_{1-4}$ alkoxy, $C_{1-4}$ haloalkoxy, $C_{1-4}$ alkylthio or phenylsulphonyl; in which $R^5$ is a group of the formula

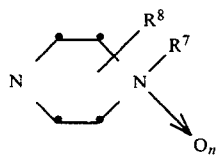

where $R^7$ is hydrogen or $C_{1-6}$ alkyl, $R^8$ is hydrogen or $C_{1-4}$ alkyl and n is 0 or 1, provided that when $R^7$ is hydrogen n is 0; and in which $R^6$ is attached to the 1, 2 or 3 position of the triazole ring and is hydrogen, $C_{1-10}$ alkyl, $C_{3-7}$ cycloalkyl, $C_{3-7}$ cycloalkyl $C_{1-4}$ alkyl, phenyl, benzyl or acyl.

Compounds of formula (I) have been found to possess useful biological properties and the invention includes a compound of formula (I) for use as a pharmaceutical and especially for use in the treatment of disorders of the central nervous system.

A preferred group of compunds of formula (I) is one in which $R^1$, $R^2$, $R^3$ and $R^4$ independently represent hydrogen, halogen or $C_{1-4}$ haloalkyl, $R^6$ is hydrogen, $C_{1-6}$ alkyl, $C_{3-7}$ cycloalkyl or $C_{3-7}$ cycloalkyl $C_{1-4}$ alkyl, $R^7$ is hydrogen or $C_{1-4}$ alkyl, $R^8$ is hydrogen and n is 0, being of the formula:

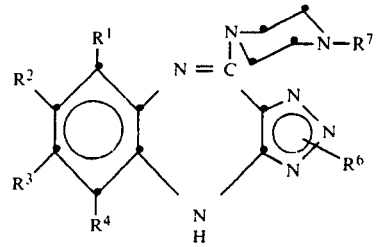

In the above general formula (I), the term "$C_{1-6}$ alkyl" means a straight or branched chain alkyl group containing 1 to 6 carbon atoms and is especially, for example, methyl, ethyl, isopropyl, propyl, butyl, sec.butyl, isobutyl, tert.butyl, pentyl or hexyl. A preferred alkyl group is "$C_{1-4}$ alkyl". The term "$C_{1-4}$ haloalkyl" means any such alkyl group substituted by one or more, preferably three halogen atoms, and is especially trifluoromethyl. The terms "$C_{1-4}$ alkoxy" and "$C_{1-4}$ alkylthio" mean any $C_{1-4}$ alkyl group attached through an oxygen or sulphur atom to a ring atom and "$C_{1-4}$ haloalkoxy" means a $C_{1-4}$ alkoxy group substituted by one or more, preferably three halogen atoms and is especially trifluoromethoxy. The term "$C_{2-4}$ alkenyl" refers to groups such as vinyl, allyl and butenyl. "$C_{3-7}$ Cycloalkyl" means a saturated ring having 3 to 7 carbon atoms in the ring such as cyclopropyl cyclobutyl, cyclopentyl, cyclohexyl or cycloheptyl, which can, in the group "$C_{3-7}$ cycloalkyl $C_{1-4}$ alkyl", be attached to the ring via an alkyl chain having 1 to 4 carbon atoms. The term "optionally substituted phenyl" means, a phenyl group which is unsubstituted or substituted by one or more groups, for example, halogen, $C_{1-4}$ haloalkyl, $C_{1-4}$ alkyl, $C_{1-4}$ alkoxy or nitro. Specific examples of such substituents include chlorine, trifluoromethyl, methyl and methoxy. The term "acyl" includes a group of the formula XCO— where X is aliphatic or aromatic and in particular where it is an alkyl group containing 1 to 10 carbon atoms, especially 1 to 4 carbon atoms. The $R^6$ group is preferably hydrogen or $C_{1-4}$ alkyl, for example methyl or ethyl, and is preferably attached at the 2-position. Preferably also n is 0.

A particularly preferred group of compounds is one of the following formula

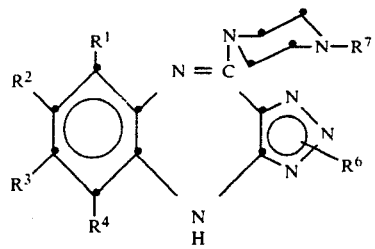

in which $R^2$ and $R^3$ independently represent hydrogen or halogen, $R^6$ is $C_{1-4}$ alkyl and $R^7$ is $C_{1-4}$ alkyl. Preferably also the $R^6$ group is attached to the triazole ring at the 2-position.

As indicated above, the compounds of the invention are useful both in their free base and acid addition salt forms. The acid addition salts are preferably the pharmaceutically acceptable, non-toxic addition salts with suitable acids, such as those with inorganic acids, for example hydrochloric, hydrobromic, nitric, sulphuric or phosphoric acids, or with organic acids, such as organic carboxylic acids, for example, glycollic, maleic, hydroxymaleic, fumaric, malic, tartaric, citric or lactic acid, or organic sulphonic acids for example methane sulphonic, ethane sulphonic, 2-hydroxyethane sulphonic, toluene-p-sulphonic or naphthalene-2-sulphonic acid. Apart from pharmaceutically acceptable acid addition salts, other salts are also included within the scope of acid addition salts such as, for example, those with picric or oxalic acid, since they may serve as intermediates in the purification of the compounds or in the preparation of other, for example, pharmaceutically acceptable, acid addition salts, or are useful for identification, characterization or purification of the bases.

According to a further aspect of the invention there is provided a process for producing a compound of formula (I) or an acid addition salt thereof, which comprises (a) reacting an amine of formula $R^5H$ with a compound of formula (II)

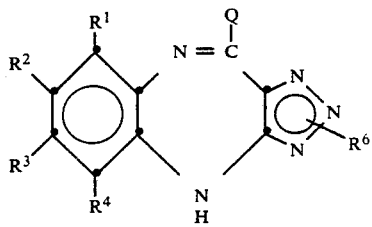
(II)

where $R^6$ is attached to the appropriate ring nitrogen and where Q represents a radical capable of being split off with the hydrogen atom of the amine $R^5H$, optionally followed when n is 0 and $R^7$ is other than hydrogen, by oxidation, or (b) ring-closing a compound of formula (III)

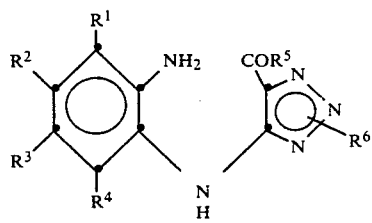
(III)

where $R^6$ is attached to the appropriate ring nitrogen, optionally followed when n is 0 and $R^7$ is other than hydrogen, by oxidation.

The above processes are of a general type previously described in the literature (see standard treatises for references to acylation, alkylation, oxidation and ring closure) and suitable Q radicals and appropriate reaction conditions can be readily chosen.

It may be mentioned, for example, that in reaction (a) the radical Q can be an amino group or a mono- or dialkyl-substituted amino group, each alkyl substituent containing 1 to 4 carbon atoms, hydroxyl, thiol, an alkoxy or alkylthio group containing 1 to 4 carbon atoms, for example a methoxy or methylthio group, or a halogen atom, especially a chlorine atom. Preferably, Q is amino ($NH_2$), hydroxyl or thiol and amino is most preferred.

When Q is amino the intermediates of formula (II) may also exist in the imino form:

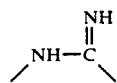

and when Q is hydroxyl or thiol, the intermediates of formula (II) may exist in their amide and thioamide forms:

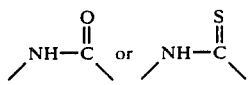

The amidines of formula (II) (Q is $NH_2$), can be in a salt form for example as the hydrochloride, and they can be reacted with amines of formula $R^5H$, optionally diluted with a solvent such as anisole, toluene, dimethylformamide or dimethylsulphoxide, and at a temperature range of 100° to 150° C. Alternatively the amidine can be converted into the corresponding amide of formula (II) (Q is OH) by alkaline hydrolysis.

When Q is hydroxyl, reaction (a) can be accomplished in the presence of titanium tetrachloride which has the ability to react with the amine of formula $R^5H$ to form a metal amine complex. Other metal chlorides such as those of zirconium, hafnium or vanadium may also be employed. The reaction is preferably carried out in the presence of an acid binding agent such as a tertiary amine, for example, triethylamine. Alternatively, the reaction can be carried out using excess of the amine of formula $R^5H$ to act as an acid-binding agent. A suitable organic solvent such as toluene or chlorobenzene can be used as a reaction medium, although it has been found that the use of anisole is particularly desirable, at least as a co-solvent, in view of its ability to form a soluble complex with $TiCl_4$.

If desired, elevated temperatures, for example up to 200° C., can be used to expedite the reaction and a preferred temperature range for carrying out the reaction is from 80° C. to 120° C.

Thioamides of formula (II) (Q is SH), iminothioethers, iminoethers or iminohalides, or other derivatives containing active Q radicals as specified above, tend to be more reactive towards the amine $R^5H$ and can usually be reacted without the necessity for the presence of $TiCl_4$, but otherwise employing the same conditions of temperature and solvent.

In reaction (b) compounds of formula (III) may be ring-closed by employing, for example, the same conditions in terms of catalyst and solvent as those described above for reaction (a) and preferably at a temperature of 150° C. to 200° C. The compounds of formula (III) may also be prepared in situ without isolation.

When the compound of formula (I) is one in which either $R^6$ or $R^7$ is other than hydrogen it is preferred that such groups are already present in the reactants, that is, the amine of formula $R^5H$, or the compounds of formula (II) or (III). However a compound in which $R^6$ or $R^7$ is hydrogen may be further reacted to provide other compounds of the invention. For example when $R^6$ is hydrogen, the compound can be reacted with $R^6X$ by conventional alkylation or acylation type methods, X being a leaving group, employing a suitable solvent and base. The group X can be a suitable reactive atom such as chlorine, bromine or iodine, or a reactive group such as tosyl or mesyl. Similarly, when $R^7$ is hydrogen, the compound can be reacted with a reagent of formula $R^7X$ in an inert solvent and in the presence of a base.

When the compound prepared by reaction (a) or (b) is one in which n is 0, and $R^7$ is other than hydrogen, it may be oxidised to provide other compounds of the invention, that is, the corresponding compound in which n is 1. Suitable oxidising agents include for example m-chloroperbenzoic acid and the reaction is preferably carried out in an inert solvent such as for example dichloromethane at a temperature of from $-10°$ C. to $+10°$ C.

The compounds of formula (I) produced by the above processes may be isolated per se or may be converted to their corresponding acid addition salts using conventional methods.

The amidines of formula (II) (Q is $NH_2$) can be prepared by condensation of a triazole of formula

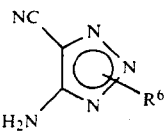

where $R^6$ is attached to the appropriate ring nitrogen, with an ortho-halonitrobenzene of formula ![structure with R1, R2, R3, R4, NO2, Z on benzene ring]

where Z is halogen, preferably fluorine, bromine or chlorine, in the presence of a base for example, sodium hydride in a solvent such as tetrahydrofuran or dimethylformamide, n-butyl lithium in tetrahydrofuran, potassium carbonate in dimethylsulphoxide or with a tetraalkyl-ammonium salt in a two-phase system, to form a nitronitrile of formula (IV)

![structure IV]  (IV)

which can be simultaneously reduced and ring-closed to the amidine of formula (II) employing for example, stannous chloride and hydrogen chloride in aqueous ethanol or, alternatively, by reduction with hydrogen and palladium/carbon or ammonium polysulphide followed by acid-catalysed ring closure.

Similarly, the amides of formula (II) (Q is OH) can be prepared by condensation of a triazole compound of formula ![structure with R9O2C, NH2, N, N, R6]

where $R^6$ is attached to the appropriate ring nitrogen, with an ortho-halonitrobenzene, as outlined above, to form a nitro ester which can be reduced to the amino ester of formula (V)

![structure V]  (V)

catalytically, employing for instance, hydrogen and palladium/carbon or chemically, employing for example, stannous chloride and hydrogen chloride in aqueous ethanol, or ammonium polysulphide. Ring closure of an amino ester of formula (V) where $R^9$ is a $C_{1-4}$ alkyl group, employing for example sodium methylsulphinyl methanide in a suitable solvent such as dimethylsulphoxide can give an amide of formula (II) (Q is OH). Alternatively, these amides can be prepared by ring closure of an amino-acid, employing for example dicyclohexylcarbodiimide (DCC) in a suitable solvent such as tetrahydrofuran. These amino-acids can be obtained for example from the esters of formula (V) by basic hydrolysis using for example sodium hydroxide in ethanol.

Triazole starting materials used in the processes described above are either known compounds, see for example Chem. & Ind. (1970) 92, J. Am. Chem. Soc. (1956) 78 5832; J. Chem. Soc. (C) (1968) 2076; J. Chem. Soc. Perkin 1 (1972) 461; J. Chem. Soc. Perkin 1 (1973) 1634; J. Chem. Soc. (C) (1968) 344; J. Am. Chem. Soc. (1957) 79 490; J. Appl. Chem. (1957) 7 109; J. Chem. Soc. (C) (1969) 152; J. Chem. Soc. (C) 1969 2379; or can be prepared by conventional techniques from known compounds. The ortho-halonitrobenzene intermediates are either commercially available or can be simply prepared from commercially available substances.

Thioamides of formula (II) (Q is SH) can be prepared by treating a solution of the corresponding amide in an anhydrous basic solvent such as for example pyridine with phosphorus pentasulphide. Similarly, the amides can be converted to iminothioethers, iminoethers or iminohalides, or other derivatives containing active Q radicals, by treatment with conventional reagents such as for example in the case of an iminochloride, phosphorus pentachloride.

Compounds of formula (II) are novel and those in which Q is hydroxyl, thiol or amino are included as an aspect of the invention. The salts of compounds in which Q is amino, such as those derived from inorganic acids for example hydrogen chloride, are particularly included.

In reaction (b), the compounds of formula (III) can be prepared in situ without isolation by reacting a compound of formula (V) with an amine of formula $R^5H$ such as by heating to a temperature between 30° C. and 120° C., for example 100° C., in a suitable solvent such as for example anisole and employing $TiCl_4$ as catalyst, or by conventional methods from compounds of formula (V), followed by ring closure to produce the compounds of the invention.

As an illustration of the preparation of representative compounds of the invention the following reaction scheme is given, in which a route for preparing a 10-(4-alkyl-1-piperazinyl)-2,4-dihydro-1,2,3-triazolo[4,5-b][1,5]benzodiazepine, is shown:

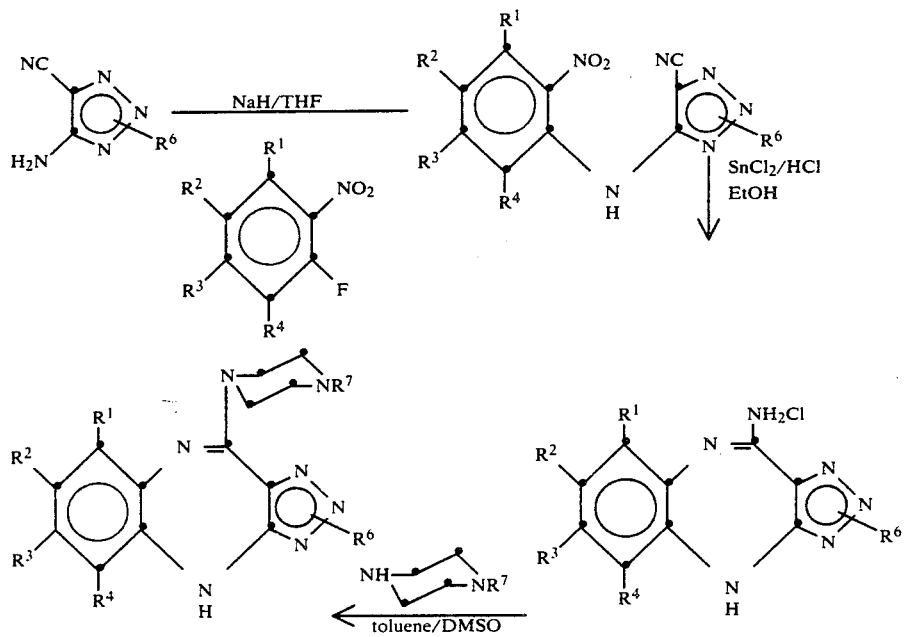

As stated previously, the compounds of the invention have useful central nervous system activity. This activity has been demonstrated in animal models using well-established procedures. In behavioural studies in mice, for instance, the compounds were observed to produce activity decrease at a dose range of 12.5 to 200 mg/kg p.o. In addition compounds have been found to be active in the spiroperidol binding test described by P. Seeman et al, in Nature 261, 717–719 (1976) and for example have an $IC_{50}$ value (the concentration of the compound required to reduce the binding of spiroperidol by 50 percent) of less than 2 μM. Thus the compounds are potent centrally acting compounds with neuroleptic, sedative or relaxant, anxiolytic or antiemetic properties. These properties, coupled with their high therapeutic index, render them useful in the treatment of mild anxiety states and certain kinds of psychotic conditions such as schizophrenia and acute mania.

The compounds of this invention are effective over a wide dosage range, the actual dose administered being dependent on such factors as the particular compound being used, the condition being treated and the type and size of mammal being treated. However, the dosage required will normally fall within the range of 0.5 to 50 mg/kg per day, for example in the treatment of adult humans, dosages of from 5 to 500 mg per day may be used.

The compounds of the invention will normally be administered orally or by injection and, for this purpose, the compounds will usually be utilised in the form of a pharmaceutical composition. Such compositions are prepared in a manner well known in the pharmaceutical art and comprise at least one active compound. Accordingly the invention includes a pharmaceutical composition comprising as active ingredient a compound of formula I or an acid addition salt thereof, associated with a pharmaceutically acceptable carrier. In making the compositions of the invention, the active ingredient will usually be mixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Some examples of suitable carriers are lactose, dextrose, sucrose, sorbitol, mannitol, starches, gum acacia, calcium phosphate, alginates, tragacanth, gelatin, syrup, methyl cellulose, methyl- and propyl-hydroxybenzoate, talc, magnesium stearate or mineral oil. The compositions of the invention may, if desired, be formulated so as to provide quick, sustained or delayed release of the active ingredient after administration to the patient.

Depending on the route of administration, the foregoing compositions may be formulated as tablets, capsules or suspensions for oral use and injection solutions for parenteral use or as suppositories. Preferably the compositions are formulated in a dosage unit form, each dosage containing from 1 to 200 mg, more usually 5 to 100 mg, of the active ingredient.

The following Examples illustrate the invention:

EXAMPLE 1

7-Fluoro-2-methyl-10-[4-methyl-1-piperazinyl]-2,4-dihydro-1,2,3-triazolo[4,5-b][1,5]benzodiazepine 10-Amino-7-fluoro-2-methyl-2,4-dihydro-1,2,3-triazolo[4,5-b][1,5]benzodiazepine hydrochloride (2.68 g) was added to a mixture of dry dimethyl sulphoxide (10 ml), toluene (10 ml) and dry N-methyl piperazine (3.3 ml), which had been degassed with nitrogen for 20 minutes. The stirred solution was then heated at 125° C. (oil-bath) under nitrogen for five hours, cooled to room temperature, and distilled water (33.3 ml) added, keeping the temperature below 25° C. After stirring at 5° C. for half an hour, the suspension obtained was filtered off and dried at 70° C. under reduced pressure to leave a yellow crystalline solid, which was recrystallised from ethyl acetate/n hexane, melting point 195°–197° C.

10-Amino-7-fluoro-2-methyl-2,4-dihydro-1,2,3-triazolo-[4,5-b][1,5]benzodiazepine hydrochloride To a slurry of 5-cyano-2-methyl-4[4-fluoro-2-nitroanilino]-1,2,3-triazole (2.62 g) in ethanol (25 ml) was added anhydrous stannous chloride (5.7 g) in concentrated hydrochloric acid (25 ml) and the solution heated at reflux for one hour, cooled and the resulting solid filtered to give a pale yellow crystalline solid; melting point 275° C.

2-Methyl-4-[4-fluoro-2-nitroanilino]-1,2,3-triazole-5-carbonitrile

To a solution of 4-amino-2-methyl-1,2,3-triazole-5-carbonitrile (1.7 g) in tetrahydrofuran (35 ml) under nitrogen, was added sodium hydride (1.0 g; 50% oil dispersion) at room temperature. After 15 minutes, 2,5-difluoronitrobenzene(2.22 g) was added to the mixture, which was stirred overnight under nitrogen. The deep red solution was then quenched in ice/water/HCl and filtered to give an orange solid. The solid was chromatographed on a magnesium silicate column using dichloromethane; the purified product recrystallised from ethyl acetate-ethanol to give an orange crystalline solid, melting point 159°–160° C.

EXAMPLE 2

6,7-Dichloro-2-methyl-10-[4-methyl-1-piperazinyl]-2,4-dihydro-1,2,3-triazolo[4,5-b][1,5]benzodiazepine 10-Amino-6,7-dichloro-2-methyl-2,4-dihydro-1,2,3-triazolo[4,5-b][1,5]benzodiazepine hydrochloride (0.84 g) was added to a mixture of dry dimethylsulphoxide (5 ml), toluene (5 ml) and N-methylpiperazine (1 ml), which had been purged with nitrogen for 20 minutes. The stirred solution was then heated at 125° C. (oil bath) under nitrogen for 16 hours, cooled to room temperature, and distilled water (10 ml) added, keeping the temperature below 25° C. After stirring at 5° C. for half an hour, the suspension obtained was filtered off and dried at 70° C. under reduced pressure to leave a yellow-brown solid which was recrystallised from ethyl acetate/n-hexane to give a yellow crystalline solid, melting point 217.5°–218.5° C.

10-Amino-6,7-dichloro-2-methyl-2,4-dihydro-1,2,3-triazolo-[4,5-b][1,5]benzodiazepine hydrochloride To a slurry of 2-methyl-4[4,5-dichloro-2-nitroanilino]-1,2,3-triazole-5-carbonitrile(1.1 g) in ethanol (10 ml) was added anhydrous stannous chloride (2.0 g) in concentrated hydrochloric acid (10 ml) and the solution heated at reflux for one hour, cooled and the resulting solid filtered and dried at 70° C. under reduced pressure to give an orange crystalline solid, recrystallised from ethanol, melting point>255° C.

2-Methyl-4[4,5-dichloro-2-nitroanilino]-1,2,3-triazole-5-carbonitrile

To a solution of 4-amino-2-methyl-1,2,3-triazole-5-carbonitrile (1.7 g) in tetrahydrofuran (40 ml) under nitrogen was added sodium hydride (1.0 g, 50% oil dispersion) at room temperature. After 15 minutes, 2,4,5-trichloronitro-benzene (3.13 g) was added to the mixture, which was stirred for six hours under nitrogen. The deep-red solution was then quenched in ice/water/HCl and filtered to leave a yellow-orange solid. The solid was chromatographed on a magnesium silicate column using dichloromethane. The purified product was recrystallised from ethanol to give an orange crystalline solid, melting point 148°–150° C.

The following compounds of formula (I) were prepared by a similar method.

7-Chloro-2-methyl-10-[4-methyl-1-piperazinyl]-2,4-dihydro-1,2,3-triazolo[4,5-b][1,5]benzodiazepine, m.p. 200°–203° C. (acetonitrile).

7-Bromo-2-methyl-10-[4-methyl-1-piperazinyl]-2,4-dihydro-1,2,3-triazolo[4,5-b][1,5]benzodiazepine. m.p. 183°–184° C. (ethyl acetate/n-hexane).

7-Trifluoromethyl-2-methyl-10-[4-methyl-1-piperazinyl]-2,4-dihydro-1,2,3-triazolo[4,5-b][1,5]benzodiazepine. m.p. 109°–111° C. (ethyl acetate/n-hexane).

2-Methyl-10-[4-methyl-1-piperazinyl]-2,4-dihydro-1,2,3-triazolo[4,5-b][1,5]benzodiazepine. m.p. 182°–184° C. (ethyl acetate/n-hexane).

7-Fluoro-2-ethyl-10-[4-methyl-1-piperazinyl]-2,4-dihydro-1,2,3-triazolo[4,5-b][1,5]benzodiazepine. m.p. 178°–180° C. (ethyl acetate/n-hexane).

7-Chloro-2-ethyl-10-[4-methyl-1-piperazinyl]-2,4-dihydro-1,2,3-triazolo[4,5-b][1,5]benzodiazepine. m.p. 180°–182° C. (ethyl acetate/n-hexane).

The following intermediates of formula (II) were prepared by the method described above.

10-Amino-7-chloro-2-methyl-2,4-dihydro-1,2,3-triazolo-[4,5-b][1,5]benzodiazepine hydrochloride. m.p.>300° C. (with decomposition) (ethanol).

10-Amino-7-bromo-2-methyl-2,4-dihydro-1,2,3-triazolo-4,5-b][1,5]benzodiazepine hydrochloride m.p. 287°–291° C. (ethanol)

10-Amino-7-trifluoromethyl-2-methyl-2,4-dihydro-1,2,3-triazolo[4,5-b][1,5]benzodiazepine hydrochloride. m.p.>275° C. (ethanol).

10-Amino-2-methyl-2,4-dihydro-1,2,3-triazolo[4,5-b][1,5]benzodiazepine hydrochloride. m.p.>270° C. (ethanol).

10-Amino-2-ethyl-7-fluoro-2,4-dihydro-1,2,3-triazolo-[4,5-b][1,5]benzodiazepine hydrochloride. m.p. 270° C. (ethanol).

10-Amino-7-chloro-2-ethyl-2,4-dihydro-1,2,3-triazolo-4,5-b][1,5]benzodiazepine hydrochloride. m.p. 270° C. (ethanol).

The following nitroanilino nitrile intermediate compounds were isolated in the preparation of the above compounds.

2-Methyl-4-[4-chloro-2-nitroanilino]-1,2,3-triazole-5-carbonitrile. m.p. 166°–168° C. (ethanol)

2-Methyl-4-[4-bromo-2-nitroanilino]-1,2,3-triazole-5-carbonitrile. m.p. 162°–164° C. (ethanol)

2-Methyl-4-[4-trifluoromethyl-2-nitroanilino]-1,2,3-triazole-5-carbonitrile. m.p. 116°–117° C. (ethanol)

2-Methyl-4-[2-nitroanilino]-1,2,3-triazole-5-carbonitrile. m.p. 144°–145° C. (ethanol)

2-Ethyl-4-[4-fluoro-2-nitroanilino]-1,2,3-triazole-5-carbonitrile. m.p. 115°–116° C. (ethanol)

2-Ethyl-4-[4-chloro-2-nitroanilino]-1,2,3-triazole-5-carbonitrile. m.p. 130°–132° C. (ethanol)

EXAMPLE 3

Tablets each containing 50 mg of active ingredient are made up as follows

| Active ingredient | 50 mg |
|---|---|
| Starch | 120 mg |
| Microcrystalline cellulose | 100 mg |
| Polyvinylpyrrolidone (as 10% solution in water) | 13 mg |
| Sodium carboxymethyl starch | 14 mg |
| Magnesium stearate | 3 mg |
| Total | 300 mg |

The active ingredient, starch and cellulose are mixed thoroughly. The solution of polyvinylpyrrolidone is mixed with the resultant powders and passed through a sieve. The granules so produced are dried and re-passed through a sieve. The sodium carboxymethyl starch and magnesium stearate are then added to the granules which, after mixing, are compressed on a tablet machine to yield tablets each weighing 300 mg.

EXAMPLE 4

Capsules each containing 100 mg of medicament are made as follows

| Active ingredient | 100 mg |
|---|---|
| Dried starch | 98 mg |
| Magnesium stearate | 2 mg |
| Total | 200 mg |

The active ingredient, starch and magnesium stearate are passed through a sieve and filled into hard gelatin capsules in 200 mg quantities.

EXAMPLE 5

Suppositories each containing 100 mg of active ingredient are made as follows

| Active ingredient | 100 mg |
|---|---|
| Saturated fatty acid glycerides to | 2,000 mg |

The active ingredient is passed through a sieve and suspended in the saturated fatty acid glycerides previously melted using the minimum heat necessary. The mixture is then poured into a suppository mould of nominal 2 g capacity and allowed to cool.

EXAMPLE 6

Suspensions each containing 50 mg of medicament per 5 ml dose are made as follows

| Active ingredient | 50 mg |
|---|---|
| Sodium carboxymethyl cellulose | 50 mg |
| Sucrose | 1.25 g |
| p-Hydroxybenzoates | 0.5 mg |
| Flavour | q.s. |
| Colour | q.s. |
| Purified water to | 5 ml. |

The medicament is passed through a sieve and mixed with the sodium carboxymethyl cellulose and sugar (dissolved in water) to form a smooth paste. The p-hydroxybenzoates, flavour and colour are dissolved in some of the water and added, with stirring. Sufficient water is then added to produce the required volume.

We claim:
1. A compound of formula

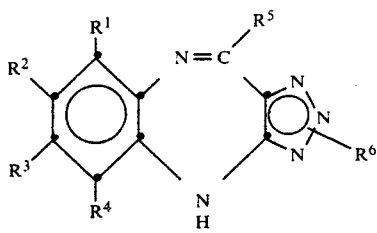

or an acid addition salt thereof; in which $R^1$, $R^2$, $R^3$ and $R^4$ independently represent hydrogen, $C_{1-4}$ alkyl, $C_{2-4}$ alkenyl, halogen, $C_{1-4}$ haloalkyl, nitro, $C_{1-4}$ alkoxy, $C_{1-4}$ haloalkoxy, $C_{1-4}$ alkylthio or phenylsulphonyl; in which $R^5$ is a group of the formula

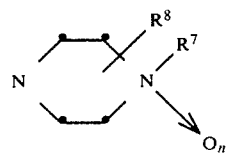

where $R^7$ is hydrogen or $C_{1-6}$ alkyl, $R^8$ is hydrogen or $C_{1-4}$ alkyl and n is 0 or 1, provided that when $R^7$ is hydrogen n is 0; and in which $R^6$ is attached to the 1, 2 or 3 position of the triazole ring and is hydrogen, $C_{1-10}$ alkyl, $C_{3-7}$ cycloalkyl, $C_{3-7}$ cycloalkyl $C_{1-4}$ alkyl, phenyl, benzyl or acyl.

2. A compound according to claim 1 in which $R^1$, $R^2$, $R^3$ and $R^4$ independently represent hydrogen, halogen or $C_{1-4}$ haloalkyl, $R^6$ is hydrogen, $C_{1-6}$ alkyl, $C_{3-7}$ cycloalkyl or $C_{3-7}$ cycloalkyl $C_{1-4}$ alkyl, $R^7$ is hydrogen or $C_{1-4}$ alkyl, $R^8$ is hydrogen and n is 0.

3. A compound according to claim 2 in which $R^6$ is hydrogen or $C_{1-4}$ alkyl.

4. A compound according to claim 3 of the formula

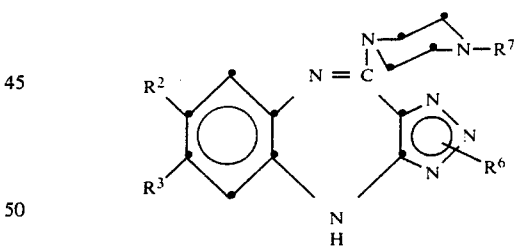

in which $R^2$ and $R^3$ independently represent hydrogen or halogen, $R^6$ is $C_{1-4}$ alkyl and $R^7$ is $C_{1-4}$ alkyl.

5. A compound according to claim 4 in which the $R^6$ group is attached to the triazole ring at the 2-position.

6. A pharmaceutical formulation useful for treating CNS disorders comprising an effective amount of a compound as defined in claim 1, or a pharmaceutically-acceptable acid addition salt thereof, and a pharmaceutically-acceptable diluent or carrier therefor.

7. A method of treating an animal including a human being, suffering from or susceptible to a CNS disorder, which comprises administering a pharmaceutically-effective amount of a compound according to claim 1 or a pharmaceutically-acceptable acid addition salt thereof.

* * * * *